United States Patent
Ríos Castañeda et al.

(10) Patent No.: US 8,268,893 B2
(45) Date of Patent: Sep. 18, 2012

(54) USE OF DAPSONE AS A NEUROPROTECTOR IN CEREBRAL INFARCTION

(75) Inventors: Luis Camílo Ríos Castañeda, México City (MX); Marina Altagracia Martínez, México City (MX); Juan Nader Kawachi, México City (MX); Jaime Kravzov Jinich, México City (MX)

(73) Assignees: Universidad Autonoma Metropolitana, Mexico City (MX); Instituto Nacional de Neurologia y Neurocirurgia Manuel Velasco Suarez, Mexico City (MX)

( * ) Notice: Subject to any disclaimer, the term of this patent is extended or adjusted under 35 U.S.C. 154(b) by 1424 days.

(21) Appl. No.: 10/565,309

(22) PCT Filed: Mar. 16, 2004

(86) PCT No.: PCT/MX2004/000018
§ 371 (c)(1),
(2), (4) Date: Sep. 19, 2006

(87) PCT Pub. No.: WO2005/007239
PCT Pub. Date: Jan. 27, 2005

(65) Prior Publication Data
US 2010/0063159 A1    Mar. 11, 2010

(30) Foreign Application Priority Data
Jul. 22, 2003 (MX) ............... PA/a/2003/006549

(51) Int. Cl.
*A01N 33/02* (2006.01)
*A61K 31/135* (2006.01)
(52) U.S. Cl. ............ 514/647; 514/579; 514/646
(58) Field of Classification Search ............ 514/183
See application file for complete search history.

(56) References Cited

U.S. PATENT DOCUMENTS

| | | | |
|---|---|---|---|
| 5,532,219 A * | 7/1996 | McGeer et al. | 514/42 |
| 2003/0045746 A1 * | 3/2003 | Jomaa | 562/11 |
| 2004/0029871 A1 * | 2/2004 | Thong et al. | 514/222.8 |

* cited by examiner

*Primary Examiner* — Jeffrey S. Lundgren
*Assistant Examiner* — Meghan Finn
(74) *Attorney, Agent, or Firm* — Egbert Law Offices, PLLC

(57) ABSTRACT

The use of dapsone is the first effective treatment against the disabling consequences associated with cerebral infarction in patients. Dapsone was evaluated as a neuroprotector in the cerebral infarction model produced by the occlusion of the middle cerebral artery in rats and in patients suffering from acute cerebral infarction caused by thromboembolism. In both studies, dapsone displayed a reduction of between 70 and 90% in the adverse effects which occur as a consequence of the infarction.

4 Claims, 3 Drawing Sheets

USE OF DAPSONE AS A NEUROPROTECTOR IN CEREBRAL INFARCTION

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to the use of dapsone as the first effective treatment against the disabling consequences associated with cerebral infarction in patients.

BACKGROUND OF THE INVENTION

For the pharmacological treatment of the brain stroke, some drugs have been historically used, with little clinical efficiency; among them, Citicoline. In a recent study, published in 2002 (Davalos A, Castillo J., Alvarez-Sabin J., Secades J J., Mercadal J., Lopez S., Cobo E., Warach S., Sherman D., Clark W M., Lozano R., Oral citicoline in acute ischemic stroke: an individual patient data pooling analysis of clinical trials. Stroke 33(12):2850-2857, 2002), it was demonstrated that this drug produced an improvement of 25% in average, three months after its administration to patients with brain stroke, while the patients that received a placebo improved 20% in average. As it can be inferred from these results, this pharmacological treatment is not capable of reducing the brain damage associated with brain stroke, in more than 20-30% in average.

On the other hand, the research and the development of new drugs to prevent the consequences of brain stroke, have produced disappointing results. In 2001, for example, the Food and Drug Administration of the United States of America, approved the use of 5 drugs against cardiac diseases, and no drug against brain stroke. This leads to the fact that there is no selective drug treatment for this serious illness.

The invention herein has as its objective to demonstrate the use of dapsone as the first efficient treatment against the disabling consequences associated with brain stroke in these patients.

Dapsone is a currently used drug, for the chemotherapy treatment of leprocy and in the prophylaxis against pneumonia by pneumocystis carinii. Considering that leprocy is a less frequent disease, the therapeutic use of dapsone has been limited recently.

Acute brain stroke is the third most common cause of death, and the main cause of disability in the world population. In view of the serious consequences that brain stroke means to the society under the terms of rehabilitation and medical care expenses, a new therapeutical agent, more efficient than the current was searched, synthesizing dapsone in as a new neuroprotective compound.

BRIEF SUMMARY OF THE INVENTION

The invention herein has as its objective to develop a product for the therapeutic use in the treatment of acute brain stroke. This disease is amply distributed in the world population, with an incidence of 500,000 to 750,000 people affected a year in the United States of America alone, thus it was decided to look for other therapeutic alternatives that are more efficient than those currently used.

In the search of a new therapeutic agent, more efficient than the current, for the pharmacological treatment of brain stroke, dapsone was synthesized as a compound with the following formula:

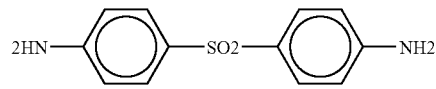

The drug dapsone has not been produced in Mexico since the eighties, and neither its raw material is produced.

DETAILED DESCRIPTION OF THE INVENTION

Figure 1:
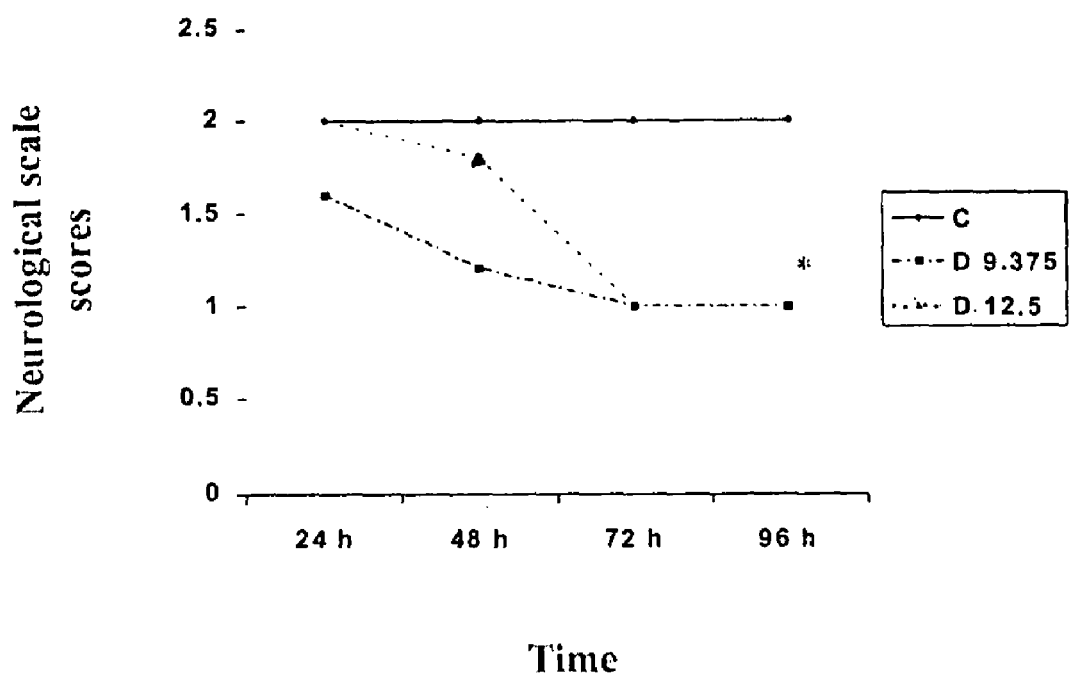
FIG. 1 shows a graph illustration of neurological scale scores.

For such reasons, the work herein demonstrates, through an experimental model, and by means of a clinical controlled trial in patients with acute brain stroke, that dapsone is efficient to prevent the adverse consequences of the disease, when administered within the first twelve hours after the ischemic event.

The pharmacological tests were performed using the experimental model of acute brain stroke for permanent obstruction of the middle cerebral artery in rats, introducing a suture thread through the internal carotid artery of the animals (Example 1). The drug was also administered to patients with acute brain stroke, that attended the Emergency Services of the National Institute of Neurology and Neurosurgery "Manuel Velasco Suarez", in Mexico City (Example 2).

The results of the experiments with rats, demonstrate that dapsone (I) at a dose of 9.325 mg/kg, had an efficacy of 93%, while at a dose of 12.5 mg/kg was 91% efficient to reduce the volume of brain damage produced by the stroke in the experimental stroke model, provoked in rats.

The efficiency results in patients, demonstrated that dapsone to a dose of 200 mg was capable of improving the neurological symptoms of patients in 67% in average.

The effective dose for dapsone, is 0.013 mmoles/kg.

No side effects were presented for the dose used.

Particularly, the following techniques are used:

Synthesis of Dapsone

Dapsone may be synthesized by different routes, but the following synthesis is offered as an example. The synthesis was performed in two steps:

1.—60 g of acetanilide were placed in an Erlenmeyer flask, and were slowly heated until all the solid material was melted. The resulted viscous liquid was cooled using an ice bath, leaving a solid material in the bottom of the flask. 165 ml of chlorosulfonic acid was added, without removing the ice. Later, the flask was removed from ice, carefully agitated and reaction was performed during 10 minutes, at the end of which the mixture of the reaction was heated again, until the total solubilization of the remaining acetanilide, letting it react again for 10 minutes more. The product was cooled and carefully poured in a container with ice and water, the precipitate was filtered and washed with cold water. The precipitate was collected, dissolved in chloroform and extracted three times with water, collecting the chloroformic phase, which was placed on an ice bath, precipitating the purified tionile chloride (reported melting point of the intermediary product: 149° C.).

2.—123.6 ml. of anhydrous nitrobenzene were placed in a reaction container, 89.2 g of aluminum chloride were added and slowly heated; to the hot mixture 41.3 g of tionile chloride were added, heating the reaction mixture to a temperature of 140-145° C., and slowly added 13 g of acetanilide, keeping the reaction temperature during two hours. At the end of this period, the raw reaction material was poured in 104 ml of acidified water with hydrochloric acid; precipitating a dark colored product, which was re-crystallized with diluted acetic acid. After the re-crystallization and filtration, the solid material was refluxed with hydrochloric acid 5N during 30 minutes, later the reaction mixture was neutralized, precipitating white crystals (raw DDS), that were re-crystallized with ethanol.

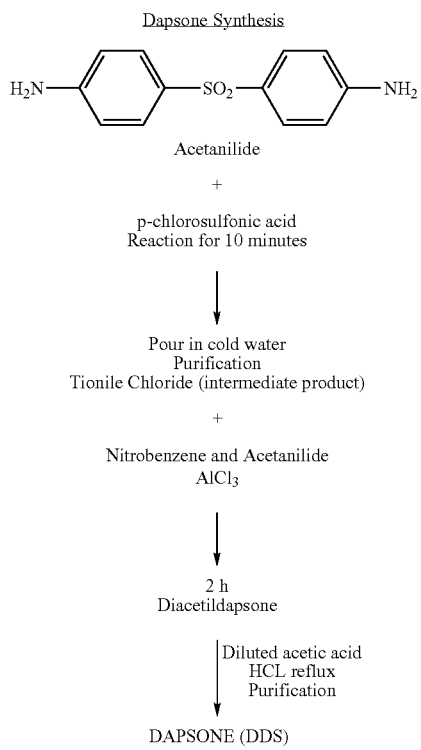

Chemical Characterization of the Synthesized Compound

To determine the authenticity of the synthesized compounds, the melting point of them was measured, resulting of 151-153° C. for the reaction intermediate tionile chloride and 172-175° C. for DDS.

The melting points reported for these compounds are 149° C., 175-176° C. for the intermediate and the DDS, respectively.

Preferential Mode to Perform the Invention

EXAMPLE 1

Evaluation of Neuroprotective Effect of Dapsone in the Acute Brain Stroke, Induced by the Occlusion of the Middle Cerebral Artery of the Rat Dapsone was evaluated as neuroprotector in the brain stroke model produced by occlusion of the middle cerebral artery. The drug was suspended in a suitable vehicle.

3 groups of 5 animals each were treated with: Saline isotonic solution (551, control group), Dapsone (12.5 mg/kg) and Dapsone (9.375 mg/kg) injected by intraperitoneal route, 30 minutes after the occlusion of the middle cerebral artery, as described below.

The permanent selective brain ischemic was produced in the animals through introducing a suture thread intraluminal through the carotid artery. All animals received continuous anesthesia during the surgical procedure with halotane 1.5%, through a face mask. Animals were placed in dorsal decubitus position, fixed and shaved in the anterior cervical region to make an incision in the middle line from the sternum towards the region of the sternohiodeous muscle, to its side rim, identifying in this side the middle rim of the sternocleidomastoideus and the superficial cervical aponeurosis in its deep leaf, same that was cut to leave exposed the common carotid blow and inside the caudal belly of the digastric. A cutting dissection of the common carotid was performed, until the hypoglose loop. The carotid bifurcation was identified, external carotid and its occipital and thyroid branches, the two latter were joined with mono-filament of 8-0 as well as with electrocoagulation for its later cut. The internal carotid was dissected in a length of approximately 5 mm and at that time the pterigo-palatine artery was identified. A microchip was placed or it was joined with mono-filament 6-0. Once the flux was stopped through these artery affluent, the mono-filament nylon 3-0 was introduced towards the internal carotid artery, through the stub of the external carotid artery, for a length of 17 mm as of the bifurcation. The wound was closed, and the animal was left to recover, with water and food ad libitum. In all cases, ischemia was verified by macroscopic observation and for the position of the thread.

Evaluation of the Neuroprotective Effect of Dapsone in Rats.

During the 96 hours after the ischemic procedure, the animals were neurologically evaluated using a functional scale, each 24 hours. This scale establishes rates from 0 to 5, according to the seriousness of the signs that the animal presents: 0=without neurological alteration; 1=difficulty to totally extend the anterior extremity; 2=circular movement towards the right; 3=falls to the right; 4=animal does not walk spontaneously and has a consciousness depressed level; 5=death.

Determination of the Tissue Volume of Damage

At the end of the 96 hours of observation, animals were sacrificed with an overdose of sodium pentobarbital by intraperitoneal route, and their brains were extracted by craniectomy. Once extracted, the brains were fixed with anhydrous alcohol during two weeks. The usual histological process was performed, as well as sections of 10 μm, storing a section each 200 μm. The latter were stained with the hematoxiline-eosine technique. All sections were observed by a pathologist, who was not aware of the treatment group, to determine, macro and microscopically, the ischemic zones.

The area of each tissue section was determined using a digital analysis system and a photographic amplifier. In all cases an amplification 1:10 was performed. Each section was assessed for 3 determinations: A) total area, including ventriculus B) Ventricular area C) Ischemic area, according to the pathologist's review. To determine the lesion volume the following formula was used:

$$V = \frac{P(0.2\,mm)}{10}$$

where P is the sum of areas (in mm$^2$), 0.2 mm is the fixed length between each section and the division between 10 is due to the amplification of each cut for volume measurement. Applying the formula, three different volumes were obtained: Total, ventricular and ischemic. The ventricular volume was subtracted from the total volume, to obtain the brain parenchyma. The latter was used as reference to obtain the lesion percentage using the ischemic volume.

EXAMPLE 2

Evaluation of the Neuroprotective Effect of Dapsone in Patients with Acute Brain Stroke This study evaluated the neuroprotector effect of dapsone in patients that, having suffered an acute brain stroke for thrombo-embolism, were admitted to the Emergency Services of the National Institute of Neurology and Neurosurgery "Manuel Velasco Suarez". Dapsone was administered in a single dose of 200 mg in suspension, orally. The suspension is kept stable in refrigeration at 4° C., for up to one month.

Dapsone was administered blinded to 15 patients, while other 15 patients were administered with an anti-acid suspension, as a placebo medication. Patients were randomly allocated into one of the treatment groups, using random numbers, generated by a pocket calculator. Both medications were administered during the first twelve hours after the brain stroke. As result of these procedures, the clinical trial was randomized, double-blind and placebo-controlled.

The evaluation of clinical signs and symptoms was performed in blind by an expert neurologist, with the NIH scale, that quantifies the intensity of disabilities caused by the brain stroke. Said scale was applied at the time the patient entered the study (day zero) and 2, 6 and 30 days after the brain stroke. A stroke is considered as moderately severe or severe, when the NIH rated a value higher than seven.

Statistical Analysis

Dapsone doses were used in the range of 1 to 12.5 mg/kg, orally in case of patients, or intraperitoneal in case of the rats.

For the neurological scale and percentage of the lesion volume in rats, the statistical significance was determined with the Kruskal-Wallis test, followed by the U test of MannWhitney.

The NIH scale results in the two groups of patients were statistically analyzed with analysis of variance analysis (ANOVA) using as co-variables the NIH scale at the admittance day (day zero), as well as the gender, age, blood pressure and other important clinical variables for the patient's performance.

Values of $\leq 0.01$ and 0.05 were taken, to determine the limit of statistical significance.

The results of the neurological evaluation in rats are shown in FIG. 1, where the scores of the neurological test as a function of time can be observed, after producing the stroke in the rats. The results are expressed as the average of 4 independent experiments. D=Dapsone (9.375 and 12.5 refers to the dose in mg/kg, ip), *p<0.05 (Kruskal-Wallis test followed by Mann-Withney test).

The data of the neurological test in rats showed that the animals treated with dapsone at the two doses employed, recovered better from the ischemic lesion, significantly, compared to the control group.

Figure 2:
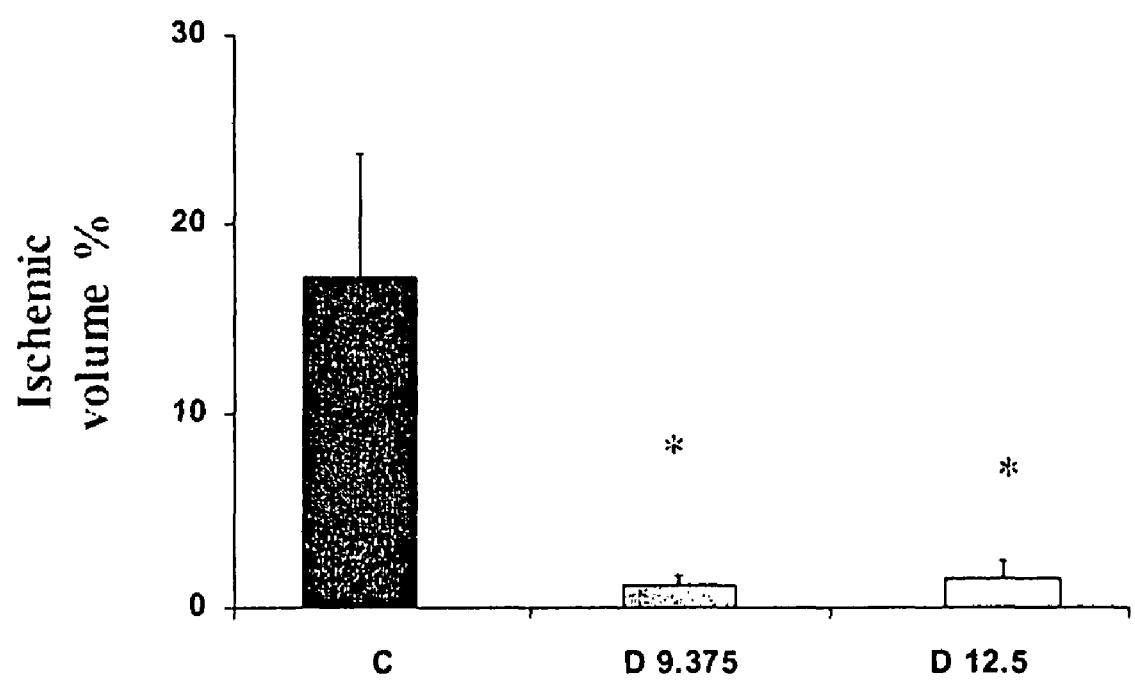
FIG. 2 shows a graph illustration of ischemic volume percentage.

The results of lesion volume are presented in FIG. 2, showing the percentage of ischemic lesion, 96 hours after producing the stroke in rats. The results are expressed as the average+/−standard error of 4 independent experiments. D=Dapsone (9.375 and 12.5 refers to the dose in mg/kg, ip), *p<0.05 (Kruskal-Wallis test, followed by Mann-Withney test).

The data obtained show that dapsone protected in 93% at the dose of 9.375 mg/kg and 90% at the dose of 12.5 mg/kg, respectively, in comparison with the control group.

Figure 3:
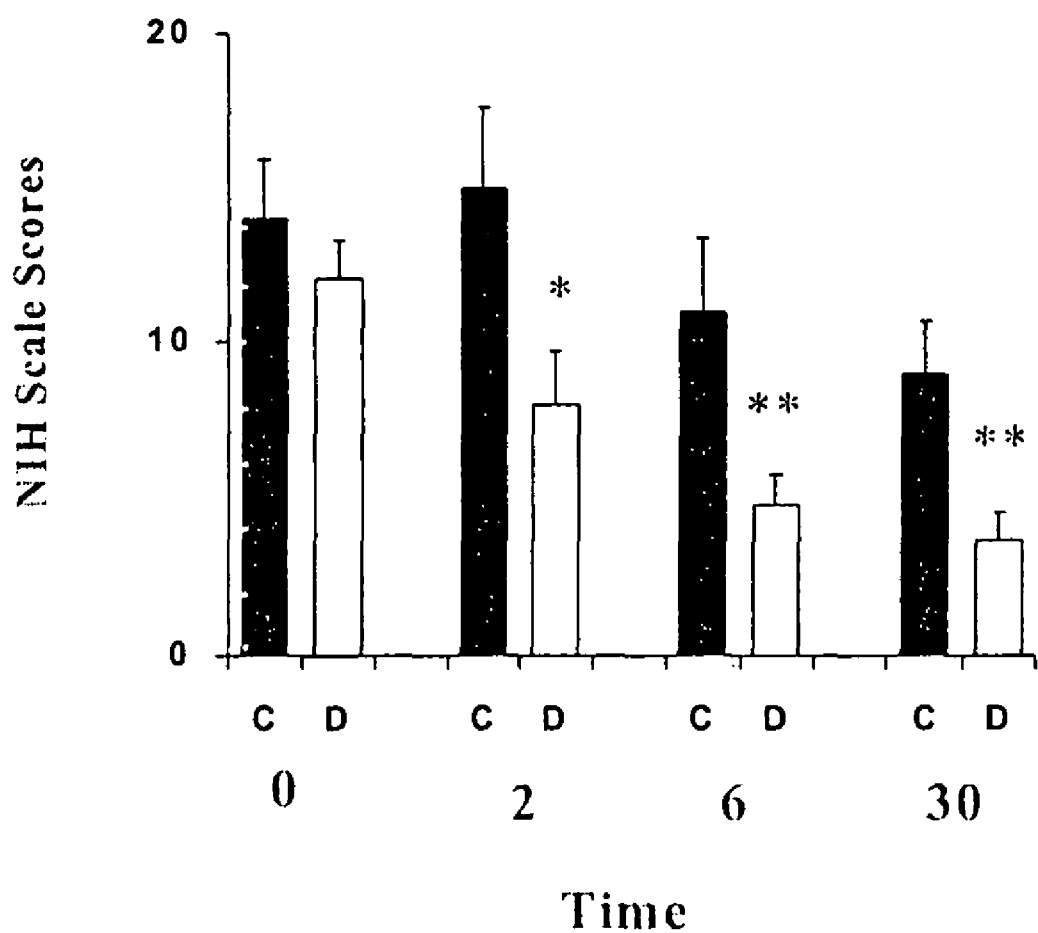
FIG. 3 shows a graph illustration of NIH scale scores.

The results in patients with acute thrombo-embolic brain stroke, are shown in FIG. 3, which presents the scores of the neurological scale (NIH) as a function of time (in days) after administering dapsone or the placebo. The results are expressed as the average of 15 patients per group +/−the standard error. D=Dapsone, *p (<0.05, **p<0.01 (Analysis of Variance test, with co-variables).

The results from patients treated with 200 mg of dapsone orally, show a significant clinical improvement. This improvement was in average 67%.

The evaluation of the neuroprotective effect of dapsone of the invention herein, may be summarized as follows:

A significant reduction in the severity of the neurological symptoms in rats, of 50% was observed, in comparison with the control group. Reductions of 93% and 90% in the lesion volume of these same animals was also observed.

Regarding the study in patients, the clinical improvement was in average 67%.

These results show that dapsone is more efficient than the currently existing drugs in the market for the treatment of acute brain stroke. This, with a preferred dose of dapsone in the range of 1 to 12.5 mg/kg, administered during the first 12 hours of the acute brain stroke, though dapsone may also be administered in repeated doses.

We claim:

1. A method of treating acute brain stroke in a brain stroke patient in need of such treatment, comprising:
    administering to the brain stroke patient Dapsone in a range of between 1 to 12.5 milligram per kilogram of the brain stroke patient's weight.
2. The method of claim 1, said step of administering comprising:
    administering the Dapsone to the brain stroke patient orally.
3. The method of claim 2, wherein the Dapsone is a suspension.
4. The method of claim 3, wherein the suspension contains 200 milligrams of Dapsone.

* * * * *